United States Patent
Strauchmann

(10) Patent No.: US 12,181,542 B2
(45) Date of Patent: *Dec. 31, 2024

(54) MR LOCAL COIL AND METHOD FOR PRODUCING SAME

(71) Applicant: Siemens Healthineers AG, Forchheim (DE)

(72) Inventor: Christina Strauchmann, Eggolsheim (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,332

(22) Filed: May 2, 2023

(65) Prior Publication Data

US 2023/0273280 A1    Aug. 31, 2023

Related U.S. Application Data

(63) Continuation of application No. 17/531,685, filed on Nov. 19, 2021, now Pat. No. 11,675,032.

(30) Foreign Application Priority Data

Nov. 20, 2020    (EP) .................................... 20208815

(51) Int. Cl.
   *G01R 33/34*    (2006.01)
   *G01R 33/385*    (2006.01)

(52) U.S. Cl.
   CPC ... *G01R 33/34007* (2013.01); *G01R 33/3858* (2013.01)

(58) Field of Classification Search
   CPC .......... G01R 33/34007; G01R 33/3858; G01R 33/341; G01R 33/34084; A61B 5/6823; A61B 5/055
   See application file for complete search history.

(56) References Cited

U.S. PATENT DOCUMENTS

| | | | |
|---|---|---|---|
| 2003/0076101 A1* | 4/2003 | Sakuma | G01R 33/34046 324/318 |
| 2006/0208734 A1 | 9/2006 | Xue et al. | |
| 2017/0067973 A1 | 3/2017 | Hyun et al. | |
| 2017/0074955 A1 | 3/2017 | Choi et al. | |
| 2020/0096582 A1 | 3/2020 | Greiser et al. | |

FOREIGN PATENT DOCUMENTS

| | | |
|---|---|---|
| DE | 102018216365 A1 | 3/2020 |
| DE | 202020104846 U1 | 9/2020 |

* cited by examiner

*Primary Examiner* — G. M. A Hyder
(74) *Attorney, Agent, or Firm* — Lempia Summerfield Katz LLC

(57) ABSTRACT

A magnetic resonance (MR) local coil, a magnetic resonance apparatus with an MR local coil, and a method for producing an MR local coil are provided. The MR local coil includes an outer casing, an antenna structure, and a frame for accommodating the antenna structure. The outer casing is embodied in a flexible manner and surrounds an inner area. The frame is embodied in a rigid manner, at least in regions, and is connected to the outer casing in a fixed manner. The antenna structure is arranged in the inner area of the outer casing and is held in position by the frame.

18 Claims, 4 Drawing Sheets

MR LOCAL COIL AND METHOD FOR PRODUCING SAME

This application is a continuation patent application of U.S. patent application Ser. No. 17/531,685 filed Nov. 19, 2021, which claims the benefit of European Patent Application No. EP 20208815.9, filed on Nov. 20, 2020, both of which are hereby incorporated by reference in their entirety.

BACKGROUND

The present embodiments relate to a magnetic resonance (MR) local coil, a magnetic resonance apparatus with an MR local coil, and a method for producing an MR local coil.

In medical technology, high soft-tissue contrasts are a particular feature of imaging using magnetic resonance (MR), also referred to as magnetic resonance tomography (MRT) or magnetic resonance imaging (MRI). In this context, excitation pulses are irradiated into an examination object, which is generally a patient, with the aid of a magnetic resonance apparatus. This triggers magnetic resonance signals in the patient. The magnetic resonance signals are received as measurement data by the magnetic resonance apparatus and used to reconstruct magnetic resonance images.

The magnetic resonance signals are often received using what are known as local coils, which are often also referred to as surface coils. Such MR local coils may include one or more MR antennas and are attached in the immediate vicinity of the patient during a magnetic resonance examination.

In order to be able to fit the MR local coil to the patient effectively, the MR local coil should be as light and flexible as possible. In order to provide a high level of patient comfort, the MR local coil should in the best case act like a simple blanket or a pillow, while simultaneously preventing the penetration of liquids and being durable when disinfected.

In order to be able to connect the flexible MR local coils to the magnetic resonance apparatus, the flexible MR local coils generally have a coil connection, in the form of a plug, for example, that may be accessed from the outside and is arranged on a flexible outer casing of the MR local coil.

SUMMARY AND DESCRIPTION

The scope of the present invention is defined solely by the appended claims and is not affected to any degree by the statements within this summary.

A reliable, sealed connection between a flexible outer casing and a coil connection is desirable. At the same time, a magnetic resonance (MR) local coil should be as simple to manufacture as possible. The present embodiments may obviate one or more of the drawbacks or limitations in the related art. For example, an MR local coil that is sealed off from the outside to the greatest possible extent and may also be manufactured with as little outlay as possible is provided.

Accordingly, an MR local coil that includes an outer casing, an antenna structure, and a frame for accommodating the antenna structure is provided. The outer casing is configured in a flexible manner and surrounds an inner area. The frame is configured in a rigid manner, at least in regions, and is connected to the outer casing in a fixed manner. The antenna structure is arranged in the inner area of the outer casing and is held in position by the frame.

The outer casing is flexible (e.g., bendable and/or geometrically adaptable in all spatial directions). In one embodiment, no noteworthy forces are necessary for this purpose. The outer casing may have a thickness of less than 5 mm (e.g., less than 2 mm).

The outer casing encloses an inner area. It is possible for further components of the MR local coil to be arranged in the inner area. For example, the antenna structure may be arranged at least partially in the inner area. The antenna structure may be flexible (e.g., bendable and/or geometrically adaptable in all spatial directions). In one embodiment, the entire MR local coil is flexible, at least in regions.

The at least one MR antenna of the antenna structure may, for example, have a round shape (e.g., an oval or circular shape) or a figure-eight shape. The at least one MR antenna may, for example, be attached to a substrate (e.g., a circuit board). The at least one MR antenna may, for example, include wires and/or coaxial cables. In one embodiment, electrical voltages and/or currents may be induced in the MR antenna by magnetic resonance signals.

At least in regions, the frame is configured so as to be rigid (e.g., not to be pliable and/or not to be flexible). The frame may be interrupted at one or more points, but is rigid in the regions between the interruption points.

The frame is connected to the outer casing in a fixed manner. For example, the frame is adhesively bonded and/or welded to the outer casing. The frame may be connected to the outer casing in a sealed manner (e.g., in a liquid-tight manner). In one embodiment, no liquids are able to penetrate into the inner area of the outer casing at the connection between the frame and the outer casing. In one embodiment, the frame enables the antenna structure to be easily installed in the inner area of the outer casing.

A further embodiment of the MR local coil makes provision for the frame to have multiple break points. As part of the production process of the MR local coil, the frame may initially only have intended break points that are then broken during production, so that the frame then has multiple break points. The intended break points in the frame may be configured as grooves, for example.

A further embodiment of the MR local coil makes provision for the frame to be connected to the outer casing by an ultrasonic welding seam. Using an ultrasonic welding seam, it is possible to produce particularly stable and/or sealed connections (e.g., air-tight and water-tight connections).

Via ultrasonic welding, it is possible, for example, to interconnect thermoplastics with a positive or material fit. Friction heat is thus usually generated in the plastic via mechanical vibrations, so that the plastics become soft, melt, and connect.

Further, the ultrasonic welding process may be easier to integrate into an electronics manufacturing environment than, for example, a thermal joining process, in which the environment is influenced due to the higher application of heat over the entire surface, but the electronics may also be damaged. Ultrasonic welding, by contrast, introduces the heat for welding materials in a targeted manner.

A further embodiment of the MR local coil makes provision for the outer casing to include an outer layer of synthetic leather and/or a fabric coated with polyurethane (PU). Such materials may be particularly resistant and/or easy to clean and/or pleasant to touch. Such material also include layers (e.g., lying in the inside), such as a padding layer and/or a sliding layer.

A padding layer (e.g., made of padding cotton) may, for example, give the MR local coil the characteristic of feeling soft and/or pillow-like. A patient may thus perceive the local coil to be more pleasant.

A sliding layer may, for example, give the MR local coil the characteristic of layers located within the shell (e.g., the antenna structure) being movable relative to one another more easily, as the layers rub against one another less strongly. As a result, it may be achieved, for example, that a restoring force that occurs when deforming the MR local coil is reduced.

In one embodiment, the outer casing may include a sliding-padding layer that both effectively pads and effectively slides. Such a sliding-padding layer may have a mesh fabric, for example. In the same manner as separate sliding and padding layers, the sliding-padding layer may be welded to the outer layer directly via the at least one ultrasonic welding seam.

A further embodiment of the MR local coil makes provision for the outer casing to have an opening for introducing the MR antenna into the outer casing. For example, the outer casing has only one opening for introducing the MR antenna into the outer casing. Due to only one opening being present, it is possible for potential leaking points in the outer shell to be reduced.

A further embodiment of the MR local coil makes provision for the frame to border the opening. The frame may be used as an aid for introducing the antenna structure into the interior of the outer shell. Via a possible arrangement directly bordering the opening, it is possible for the introduction of the antenna structure into the interior of the outer shell to take place in a particularly simple manner.

A further embodiment of the MR local coil makes provision for the outer casing to have a flat top side, where the outer casing has a flat bottom side opposite the top side. The top side and the bottom side are connected by multiple end faces, where the opening is attached to one of the end faces.

In one embodiment, the interior of the outer casing is located between the top side and the bottom side of the outer casing. The multiple end faces may each form an edge of the MR local coil. A corner may be configured where two edges meet. In one embodiment, the opening only extends over part of the end face or the edge of the MR local coil. In one embodiment, the extension of the opening amounts to less than half the length of the end face or the edge of the MR local coil. Thus, the opening may have small dimensions, so that the risk of a leak in the MR local coil may be reduced.

A further embodiment of the MR local coil makes provision for the multiple end faces to have a circumferentially uniform outer seam (e.g., an ultrasonic welding seam). For example, the outer seam may run along the edges and corners of the MR local coil. In one embodiment, the outer seam is uniform over the entire region of the corners and edges of the MR local coil with the exception of the region of the opening. As a result, the MR local coil may be perceived as particularly pleasant and valuable.

A further embodiment of the MR local coil makes provision for the frame to have a guide structure that interacts with a matching structure of the antenna structure such that the antenna structure is held in position within the outer casing.

Further, during the production of the MR local coil, the guide structure may be used to bring the antenna structure into the interior of the outer casing in a defined manner. The guide structure may include a groove and/or tongue, for example, along which the antenna structure preferably may be introduced into the interior of the outer casing during the production of the MR local coil.

A further embodiment of the MR local coil makes provision for the antenna structure to have a groove and/or tongue, via which the antenna structure is held in position in the inner area of the outer casing. For example, a tongue of the guide structure may engage into a groove of the antenna structure. In one embodiment, a tongue of the antenna structure may engage into a groove of the guide structure.

In one embodiment, keeping the antenna structure in position includes the prevention of a displacement of the antenna structure along at least one direction parallel with the top side and/or bottom side of the outer casing.

A further embodiment of the MR local coil makes provision for the MR local coil to include a cover that is detachably fastened to the outer casing in the region of the frame.

In one embodiment, the cover is configured to protect the inner area of the outer casing (e.g., to seal the inner area of the outer casing off). A detachable fastening of the frame to the outer casing may take place with the aid of screws, for example.

A further embodiment of the MR local coil makes provision for the frame to be clamped by the cover. In one embodiment, this achieves a particularly effective sealing-off of the inner area of the outer casing.

Further, a magnetic resonance apparatus with at least one MR local coil, as has been described above, is provided. The advantages of the proposed MR local coil substantially correspond to the advantages of the magnetic resonance apparatus. Features, advantages, or alternative embodiments mentioned in the description of the MR local coil may also be transferred to the magnetic resonance apparatus.

Further, a method for producing an MR local coil described above is provided, where the frame is broken at the multiple break points and the antenna structure is introduced into the outer casing along the break points.

BRIEF DESCRIPTION OF THE DRAWINGS

Parts that correspond to one another are provided with the same reference characters in all the figures.

DETAILED DESCRIPTION

Figure 1:
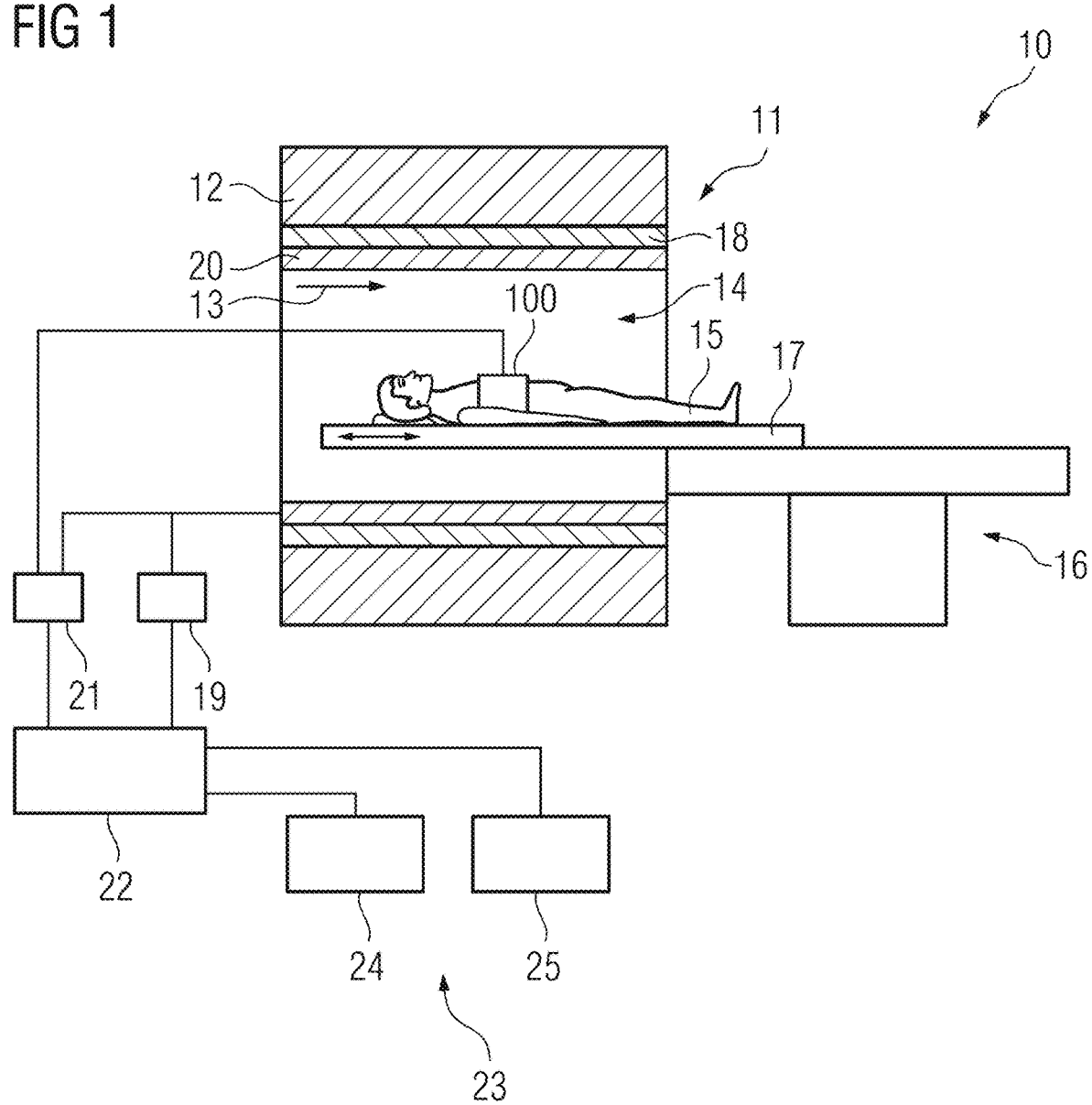
FIG. 1 shows one embodiment of a magnetic resonance apparatus with a magnetic resonance (MR) local coil.

FIG. 1 shows a schematic representation of one embodiment of a magnetic resonance apparatus 10. The magnetic resonance apparatus 10 includes a magnet unit 11 that has a main magnet 12 for generating a strong main magnetic field 13 that, for example, is constant over time. The magnetic resonance apparatus 10 also includes a patient receiving region 14 for accommodating a patient 15. In the present exemplary embodiment, the patient receiving region 14 is configured in the shape of a cylinder and is cylindrically surrounded by the magnet unit 11 in a circumferential direction. In principle, however, an embodiment of the patient receiving region 14 deviating therefrom may be provided. The patient 15 may be pushed by a patient positioning apparatus 16 of the magnetic resonance apparatus 10 into the patient receiving region 14. For this purpose, the patient positioning apparatus 16 has a patient table 17 that is configured to be movable within the patient receiving region 14.

The magnet unit 11 also has a gradient coil unit 18 for generating magnetic field gradients that are used for position encoding during an imaging process. The gradient coil unit 18 is controlled by a gradient control unit 19 of the magnetic resonance apparatus 10. The magnet unit 11 also includes a radiofrequency antenna unit 20 that, in the present exemplary embodiment, is configured as a body coil that is integrated in the magnetic resonance apparatus 10 in a fixed manner. The radiofrequency antenna unit 20 is configured to excite atomic nuclei. The excitation is established in the main magnetic field 13 generated by the main magnet 12. The radiofrequency antenna unit 20 is controlled by a radiofrequency antenna control unit 21 of the magnetic resonance apparatus 10 and radiates high-frequency magnetic resonance sequences into an examination space that is substantially formed by a patient receiving region 14 of the magnetic resonance apparatus 10. The radiofrequency antenna unit 20 is also configured to receive magnetic resonance signals.

The magnetic resonance apparatus 10 has a system control unit 22 for controlling the main magnet 12, the gradient control unit 19, and for controlling the radiofrequency antenna control unit 21. The system control unit 22 centrally controls the magnetic resonance apparatus 10 (e.g., performing a predetermined imaging gradient echo sequence).

Additionally, the magnetic resonance apparatus 10 includes a flexible MR local coil 100 that is arranged immediately on the patient 15. The MR local coil 100 includes at least one magnetic resonance antenna and is configured to receive magnetic resonance signals using the at least one magnetic resonance antenna. In one embodiment, however, the MR local coil 100 is also configured for transmitting high-frequency magnetic resonance sequences, in the same manner as the radiofrequency antenna unit 20. The received magnetic resonance signals are transferred to the radiofrequency antenna control unit 21.

Additionally, the system control unit 22 includes an evaluation unit (not shown in more detail) for evaluating the magnetic resonance signals that are detected during the magnetic resonance examination. In addition, the magnetic resonance apparatus 10 includes a user interface 23 that is connected to the system control unit 22. Control information such as imaging parameters, for example, as well as reconstructed magnetic resonance images may be displayed to medical operating personnel on a display unit 24 (e.g., on at least one monitor) of the user interface 23. Further, the user interface 23 has an input unit 25 that may be used by the medical operating personnel to enter information and/or parameters during a measurement procedure.

Figure 2:
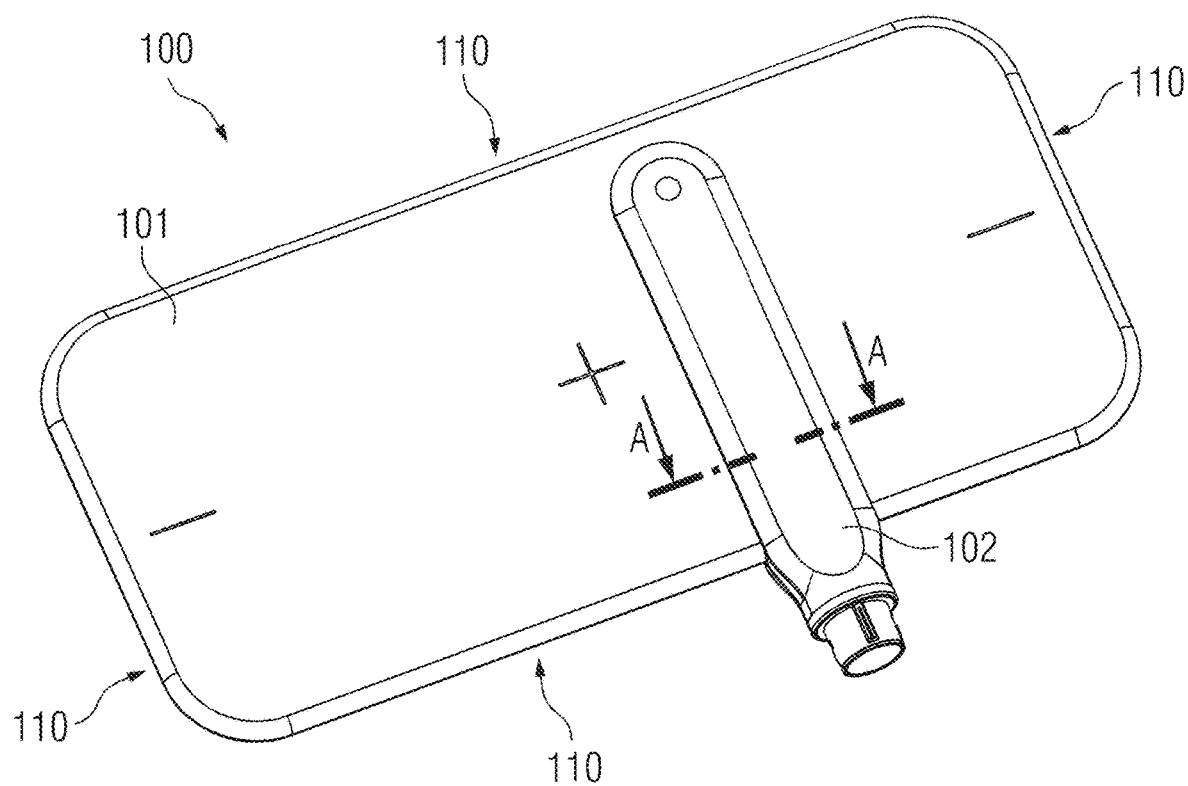
FIG. 2 shows one embodiment of an MR local coil in a perspective representation.
Figure 3:
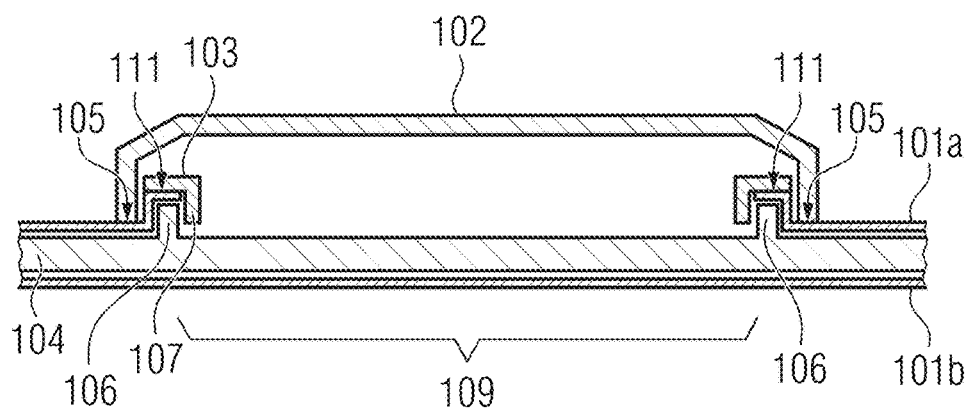
FIG. 3 shows a cross-section through one embodiment of an MR local coil.

FIG. 2 shows an exemplary MR local coil 100 with an outer casing 101 and a cover 102. The outer casing 101 includes, for example, an artificial leather and/or a PU-coated fabric or consists thereof. The cross-section indicated here, section A-A, is shown in FIG. 3.

The outer casing 101 has a flat top side 101*a* and an opposite flat bottom side 101*b*. An inner area of the outer casing 101 or of the MR local coil 100 lies therebetween. The top side 101*a* is connected to the bottom side 101*b* at four end faces 110 shown in FIG. 2.

The MR local coil also includes a frame 103 that is connected at the areas 111 to the top side 101*a* of the outer casing 101 in a fixed manner, and an antenna structure 104 that includes at least one MR antenna and is arranged in the inner area of the outer casing. The connection at the areas 111 may be produced, for example, via ultrasonic welding, so that the frame 103 is connected to the outer casing 101 by an ultrasonic welding seam.

The frame 103 is configured to accommodate the antenna structure 104 and holds the antenna structure 104 in position. To this end, the frame 103 includes a guide structure 107, and the antenna structure 104 includes a corresponding matching structure 106. The guide structure 107 (e.g., in the form of a tongue) interacts with the matching structure 106 (e.g., in the form of a tongue), such that the antenna structure 104 is held in position in the inner area of the outer casing 101. For example, the antenna structure 104 thus cannot slip to the side.

Figure 4:
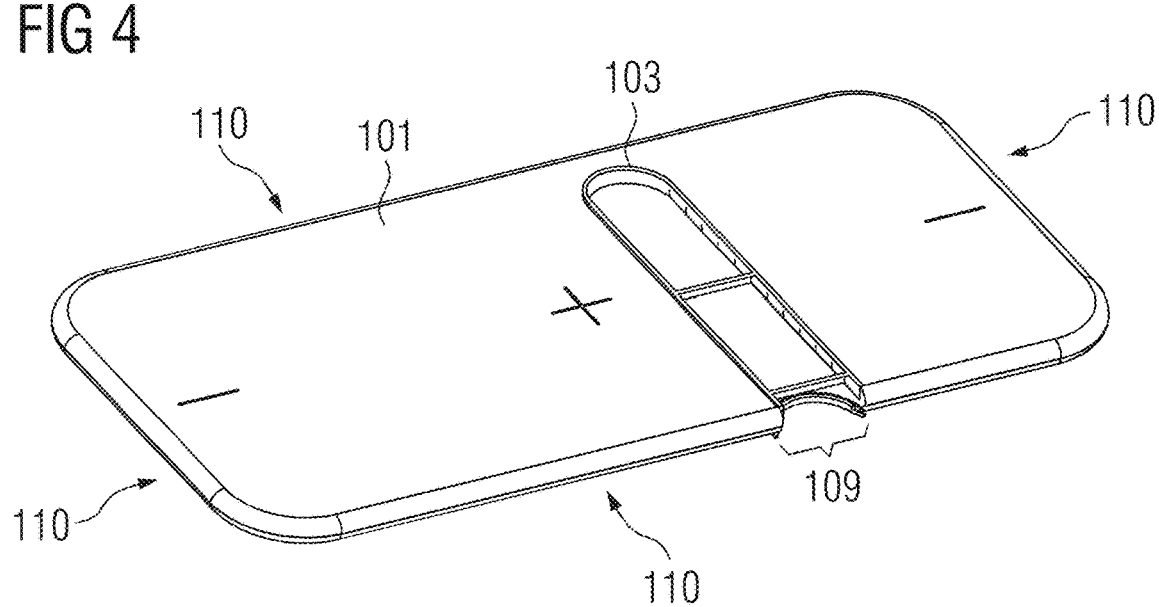
FIG. 4 shows one embodiment of an outer casing with a frame for accommodating an antenna structure.
Figure 5:
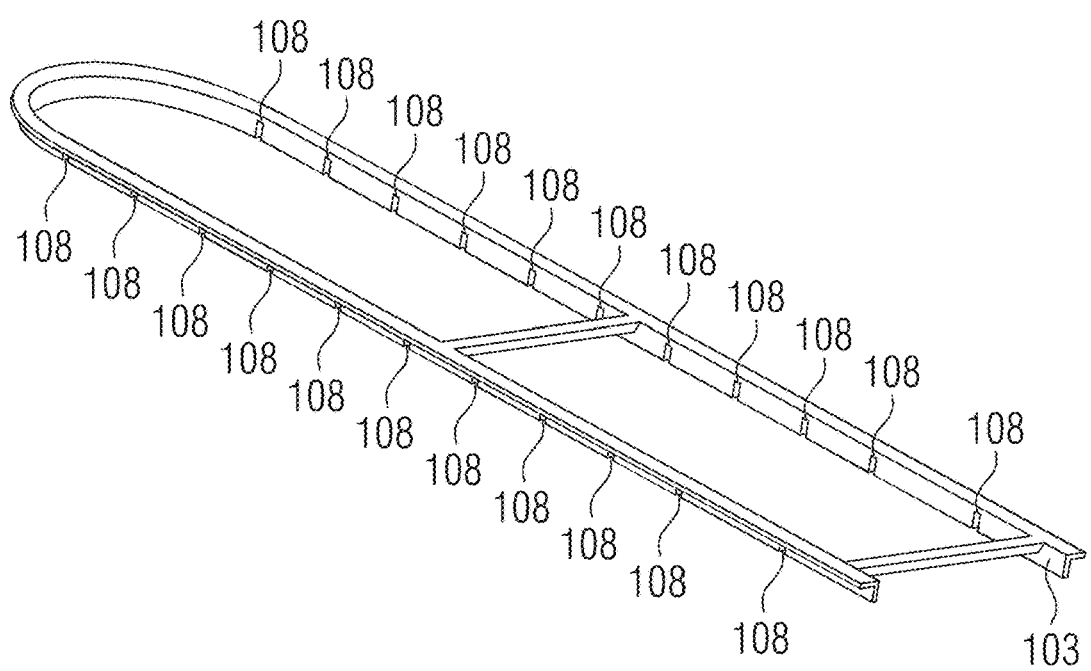
FIG. 5 shows one embodiment of a frame for accommodating an antenna structure.

The frame 103 is shown in more detail in FIGS. 4 and 5. During the manufacturing process, the frame 103 initially still includes intended break points 108, but these are broken during the course of the manufacturing process, so that the frame 103 has multiple break points. The frame 103 is therefore configured as rigid in regions between the break points.

The frame 103 shown in FIGS. 4 and 5 has two crossbars. These are able to reinforce the frame 103, so that during the production of the MR local coil 100 (e.g., while the frame 103 is being welded onto the outer casing 101), the MR local coil 100 is easier to handle. In one embodiment, the two crossbars have further intended break points at two ends (e.g., at the transition to the rest of the frame). By breaking the frame 103 at these intended break points 108, the crossbars may be easily removed, which produces a particularly large opening for inserting the antenna structure 104.

As shown in FIGS. 3 and 4, on one of the multiple end faces 110, the outer casing 101 has an opening 109 for introducing the antenna structure 104 into the inner area of the outer casing 101. In this context, the frame 103 borders the opening 109. Beyond the opening 109, the end faces 110 have a circumferentially uniform outer seam. The outer seam may be an ultrasonic welding seam, for example.

The cover 102 shown in FIGS. 2 and 3 is detachably fastened to the outer casing 101 in the region of the frame 103. In this context, the frame 103 is clamped by the cover 102.

Figure 7:
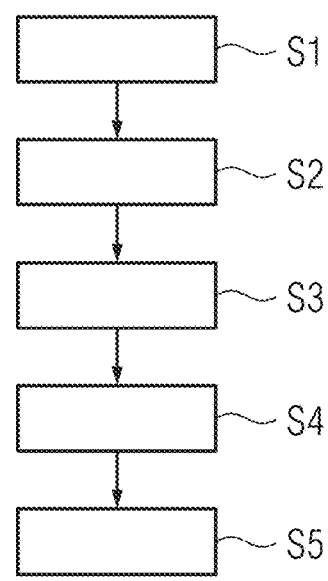
FIG. 7 shows a block diagram of one embodiment of a method for producing an MR local coil.

FIG. 7 shows a flow diagram of one embodiment of a method for an MR local coil.

Using ultrasonic welding, the outer casing 101 (e.g., including various lining materials) is generated in S1. In this context, a fully closed outer seam, or an outer seam that is only interrupted in the region of the housing cover, is produced in the visible region of the MR local coil (see FIG. 4). In one embodiment, the act S1 may be performed later in the production process (e.g., only after S2).

In the region of the cover 102, which is installed later, in S2, the frame 103 is welded onto the outer casing 101 (e.g., including various lining materials and/or padding layers and/or sliding layers) using ultrasonic welding, whereby the various materials are connected to the frame in a fixed manner. The frame 103 is shaped such that the frame 103 provides as much space as is needed for the welding process, and at the same time is as intricate as possible.

Once the frame 103 is welded to the outer casing 101 in a fixed manner, in S3, the frame 103 is broken down into multiple individual parts at intended break points 108 in the welded-on state. For example, any stabilizing crossbars of the frame 103 may be removed. This produces a flexible defined opening to the inner area of the outer casing 101, despite the outer casing 101 being configured as rigid in regions. The more intended break points 108 the frame 103 has, the more flexible the opening is.

Figure 6:
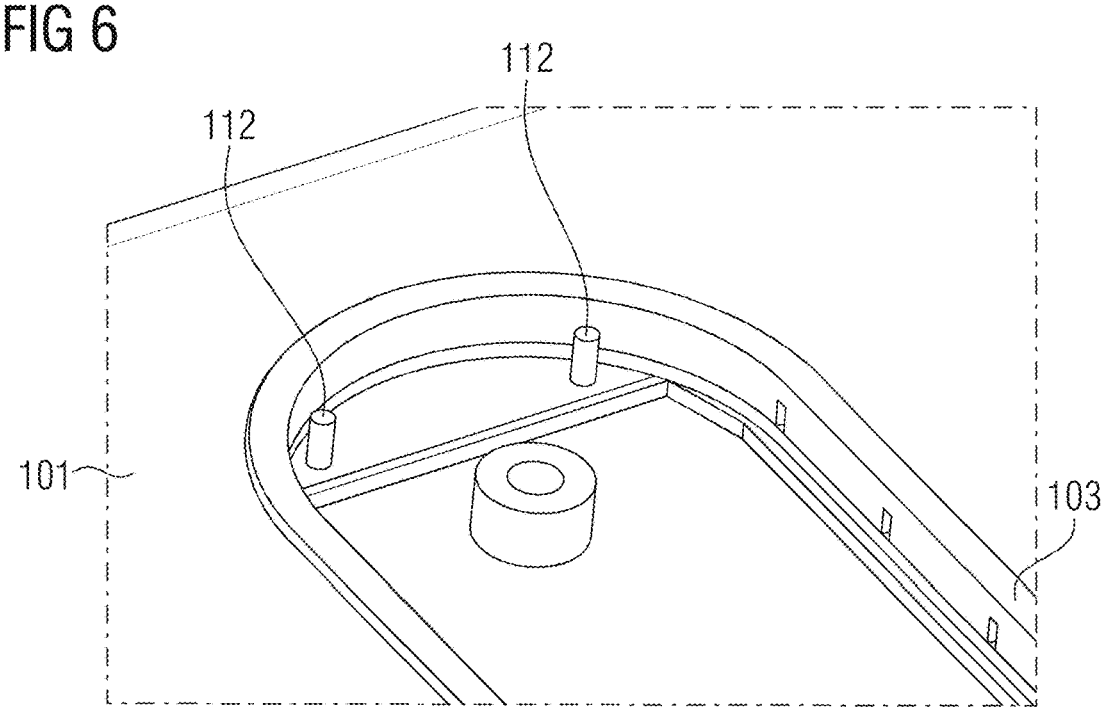
FIG. 6 shows a detail view of one embodiment of an outer casing with a frame.

The prepared antenna structure 104 is threaded through this opening, along the break points and into the outer casing 101 in S4. The threaded-in antenna structure 104 contains matching pieces 106 and 112 that rest against the frame 103 broken in a defined manner (see FIG. 3 and FIG. 6).

Subsequently, in S5, the cover 102 is screwed on, and the frame 103, which is broken in a controlled manner, is clamped in a defined manner as a result. By way of the frame 103, it is thus provided that the outer casing 101 is not able to slip out of the clamping.

As shown in FIG. 3, by screwing on the cover 102, the outer casing 101 is squeezed in the edge region in a defined manner, and thus, a seal is additionally implemented.

In summary, it may be seen that, in the proposed MR local coil 100, there is no need for an additional opening for introducing the antenna structure 104 into the outer casing 101, which would have to be retroactively closed off again in a further act, by ultrasonic welding or adhesive bonding, for example.

A further advantage may be given by the final product having a uniform outer seam and, for example, no transition being necessary in the seam (e.g., in a transition from inner seam to outer seam), and thus also not being visible from the outside.

In addition, such a seam may be more robust than any divided outer seam, as a closing seam would have to perfectly meet the rest of the outer seam. The uniform outer seam allows the product to appear more valuable and an additional work step is omitted.

The MR local coil 100 described in detail above, the magnetic resonance apparatus 10, and the method are merely exemplary embodiments, which may be modified by a person skilled in the art in many ways without departing from the scope of the invention. Further, the use of the indefinite articles "a" or "an" does not exclude the possibility that the features in question may also be present more than once. Similarly, the expression "unit" does not preclude the components in question consisting of a plurality of interacting subcomponents which may also be spatially distributed if necessary.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance (MR) local coil comprising:
   an outer casing that is configured in a flexible manner and surrounds an inner area;
   a frame for accommodating an antenna structure, the frame having multiple break points and being configured in a rigid manner, at least in regions between the break points, and being connected to the outer casing in a fixed manner, the break points being points where the frame is broken during manufacturing; and
   the antenna structure comprising at least one MR antenna that is arranged in the inner area of the outer casing and is held in position by the frame.

2. The MR local coil of claim 1, wherein the break points are formed by a breaking of intended break points.

3. The MR local coil of claim 1, wherein the frame is connected to the outer casing by an ultrasonic welding seam.

4. The MR local coil of claim 1, wherein the outer casing comprises an artificial leather, a PU-coated fabric, or the artificial leather and the PU-coated fabric.

5. The MR local coil of claim 1, wherein the outer casing has an opening for introducing the at least one MR antenna into the inner area of the outer casing.

6. The MR local coil of claim 5, wherein the frame borders the opening.

7. The MR local coil of claim 5, wherein the outer casing has a flat top side,
   wherein the outer casing has a flat bottom side opposite the flat top side,
   wherein the flat top side and the flat bottom side are connected by multiple end faces, and
   wherein the opening is attached to one of the multiple end faces.

8. The MR local coil of claim 7, wherein the multiple end faces have a circumferentially uniform outer seam.

9. The MR local coil of claim 8, wherein the outer seam is an ultrasonic welding seam.

10. The MR local coil of claim 1, wherein the frame has a guide structure that interacts with a matching structure of the antenna structure such that the antenna structure is held in position in the inner area of the outer casing.

11. The MR local coil of claim 1, wherein the antenna structure has a groove, a tongue, or the groove and the tongue via which the antenna structure is held in position within the outer casing.

12. The MR local coil of claim 1, wherein the MR local coil comprises a cover that is detachably fastened to the outer casing in the region of the frame.

13. The MR local coil of claim 12, wherein the frame is clamped by the cover.

14. A magnetic resonance apparatus comprising:
    at least one MR local coil, an MR local coil of the at least one MR local coil comprising:
        an outer casing that is configured in a flexible manner and surrounds an inner area;
        a frame for accommodating an antenna structure, the frame having multiple break points and being configured in a rigid manner, at least in regions, and being connected to the outer casing in a fixed manner, the break points being points where the frame is broken during manufacturing; and
        the antenna structure comprising at least one MR antenna that is arranged in the inner area of the outer casing and is held in position by the frame.

15. The magnetic resonance apparatus of claim 14, wherein the frame is configured in the rigid manner at least in regions between the break points.

16. The magnetic resonance apparatus of claim 14, wherein the break points are formed by a breaking of intended break points.

17. The magnetic resonance apparatus of claim 14, wherein the frame is connected to the outer casing in a liquid-tight manner.

18. A method for producing a magnetic resonance (MR) local coil, the MR local coil comprising an outer casing that is configured in a flexible manner and surrounds an inner area, a frame for accommodating an antenna structure, the frame being configured in a rigid manner, at least in regions, and being connected to the outer casing in a fixed manner, and the antenna structure comprising at least one MR antenna that is arranged in the inner area of the outer casing and is held in position by the frame, wherein the frame has multiple intended break points, the method comprising:

breaking the frame at the multiple intended break points; and introducing the antenna structure into the inner area of the outer casing along the multiple break points.

* * * * *